United States Patent [19]

Ito et al.

[11] Patent Number: 5,670,379
[45] Date of Patent: Sep. 23, 1997

[54] CHROMATOGRAPH SYSTEM AND METHOD OF USE

[75] Inventors: Masahito Ito, Katsuta; Junkichi Miura, Hitachi; Yoshio Fujii; Hiroshi Satake, both of Katsuta; Mitsuo Ito, Ibaraki-ken; Fuminori Umesato, deceased, late of Ibaraki-ken, all of Japan, by Setsuko Umesato, heiress

[73] Assignees: Hitachi, Ltd., Tokyo; Hitachi Instruments Engineering Co., Ltd., Katsuta, both of Japan

[21] Appl. No.: 372,708

[22] Filed: Jan. 13, 1995

Related U.S. Application Data

[63] Continuation of Ser. No. 61,130, May 13, 1993, abandoned.

[30] Foreign Application Priority Data

May 19, 1992 [JP] Japan ................. 4-125895

[51] Int. Cl.$^6$ ..................................... G01N 30/02
[52] U.S. Cl. ............... 436/161; 73/23.22; 73/23.36; 73/61.52; 95/82; 96/103; 210/198.2; 210/656; 422/70; 422/89; 436/66
[58] Field of Search ............. 422/68.1, 70, 89, 422/67; 436/161, 66; 210/656, 198.2; 73/61.52, 61.58, 23.22, 23.36; 96/103; 95/82; 364/497, 498

[56] References Cited

U.S. PATENT DOCUMENTS

| | | | |
|---|---|---|---|
| 3,898,837 | 8/1975 | Boege | 73/23.36 |
| 4,197,576 | 4/1980 | Martin Sanchez | 364/106 |
| 4,674,323 | 6/1987 | Rulf et al. | 422/70 |
| 4,802,981 | 2/1989 | Kenney et al. | 210/198.2 |

FOREIGN PATENT DOCUMENTS

| | | |
|---|---|---|
| 4130271 | 5/1992 | Japan . |
| 4331369 | 11/1992 | Japan . |

OTHER PUBLICATIONS

Dolan, John W. Troubleshooting LC Systems, The Humana Press Inc. Clifton NJ 1989 p. 18, 22–24, 74.

Primary Examiner—Jill Warden
Assistant Examiner—Jan M. Ludlow
Attorney, Agent, or Firm—Kenyon & Kenyon

[57] ABSTRACT

A chromatograph system with improved automation is provided. In the chromatograph system of one embodiment, a regression line is set between retention times of predetermined peaks measured at each run in the past for a standard sample having known components. Referring to this regression line, the peak identifying condition, i.e., time window, is corrected. In another embodiment, there is provided a chromatograph apparatus having a function of estimating a limited life time of a system component. The analyzed results of the chromatograph system can thus be improved.

29 Claims, 3 Drawing Sheets

CHROMATOGRAPH SYSTEM AND METHOD OF USE

This application is a continuation of application Ser. No. 08/061,130, filed 13 May 1993, now abandoned.

BACKGROUND OF THE INVENTION

The present invention relates to a chromatograph system.

Automation in chromatograph systems has been long desired. There is disclosed in JP-A-1-250060 a chromatograph system which automatically determines optimum analysis conditions in short time. According to this system, a plurality of preset analysis conditions and analysis data (retention times, peak dispersions, detector response times, and the like) of a plurality of kinds of sample component compounds separated under various analysis conditions are stored in a memory in advance. In analyzing a new sample, upon input of a desired resolution rate of a particular compound of the new sample, one of the analysis conditions suitable for analyzing the particular compound at the desired rate is selected by reading the stored analysis data from the memory and processing it in a predetermined manner. In this system, the analysis data may be stored in the memory in the form of spreadsheet, allowing addition and/or correction of the data.

There is also disclosed in U.S. patent application Ser. No. 07/836,599 filed on Feb. 18, 1992, now abandoned, corresponding to JP-A-4-331369 a chromatograph system which automatically identifies component compounds of a sample. JP-A-4-331369 was laid-open in Japan before the priority period of this application. According to this system, peaks of component compounds to be analyzed are identified by using chromatogram data of a standard sample with known components, and the width of a time window of each peak is pre-set. The windows are used for identifying the components of an unknown sample based upon its chromatogram. With this system, it is not necessary for an operator to enter the retention time of each component. The method of separating and identifying an unknown sample in this way is called a time window method.

Setting time windows is carried out at each run. During each run, thirty to one hundred unknown samples are analyzed in a general case. At each run, a standard sample is analyzed to set time windows, and thereafter, all unknown samples are sequentially analyzed without any interruption.

There is also disclosed in U.S. patent application Ser. No. 07/763,203, now abandoned, corresponding to JP-A-4-130271 a chromatograph system which automatically displays the degree of deterioration of the column, eluent, derivating reagent, and the like to alarm the operator. With this system, the deterioration is judged, for example, from whether a standard retention time of a particular peak of a standard sample at each run becomes shorter or longer than a predetermined time period.

SUMMARY OF THE INVENTION

It is an object of the present invention to provide a chromatograph system with advanced automation.

It is another object of the present invention to provide a chromatograph system capable of analyzing with high reliability.

In order to achieve at least one of the above objects of the present invention, the conditions for identifying the peaks of a chromatogram are updated by referring to the previous analysis results stored in a memory. According to one embodiment, in a chromatograph system using the time window method whereby the peak identifying conditions are set by using a standard sample at each run, i.e., for each batch of unknown samples, a regression line regarding retention times of predetermined peaks measured at each run is obtained, and the peak identifying conditions are time sequentially corrected by referring to the regression line. The regression line indicates a run-to-run variation in retention time of the predetermined peaks.

According to another aspect of the present invention, a replacement time of a component having a limited life time in the chromatograph system is notified in advance to an operator. A column which is one of the system components has an intimate relationship between its life time and column pressure (resistance). The pressure can be used therefore as an index for the life time management. Conventionally, the pressure is monitored always to judge that the life time of the column came to the end when the pressure reached a predetermined value. The present inventors have found that there is a fixed rule of a column pressure change with the number of analyzed samples, i.e., with the lapse time from the start of using the column. This rule is applied to a change in measured column pressures to estimate the future column pressure and hence the column life time.

DETAILED DESCRIPTION

Embodiments of the present invention will be described with reference to the accompanying drawings.

Figure 1:
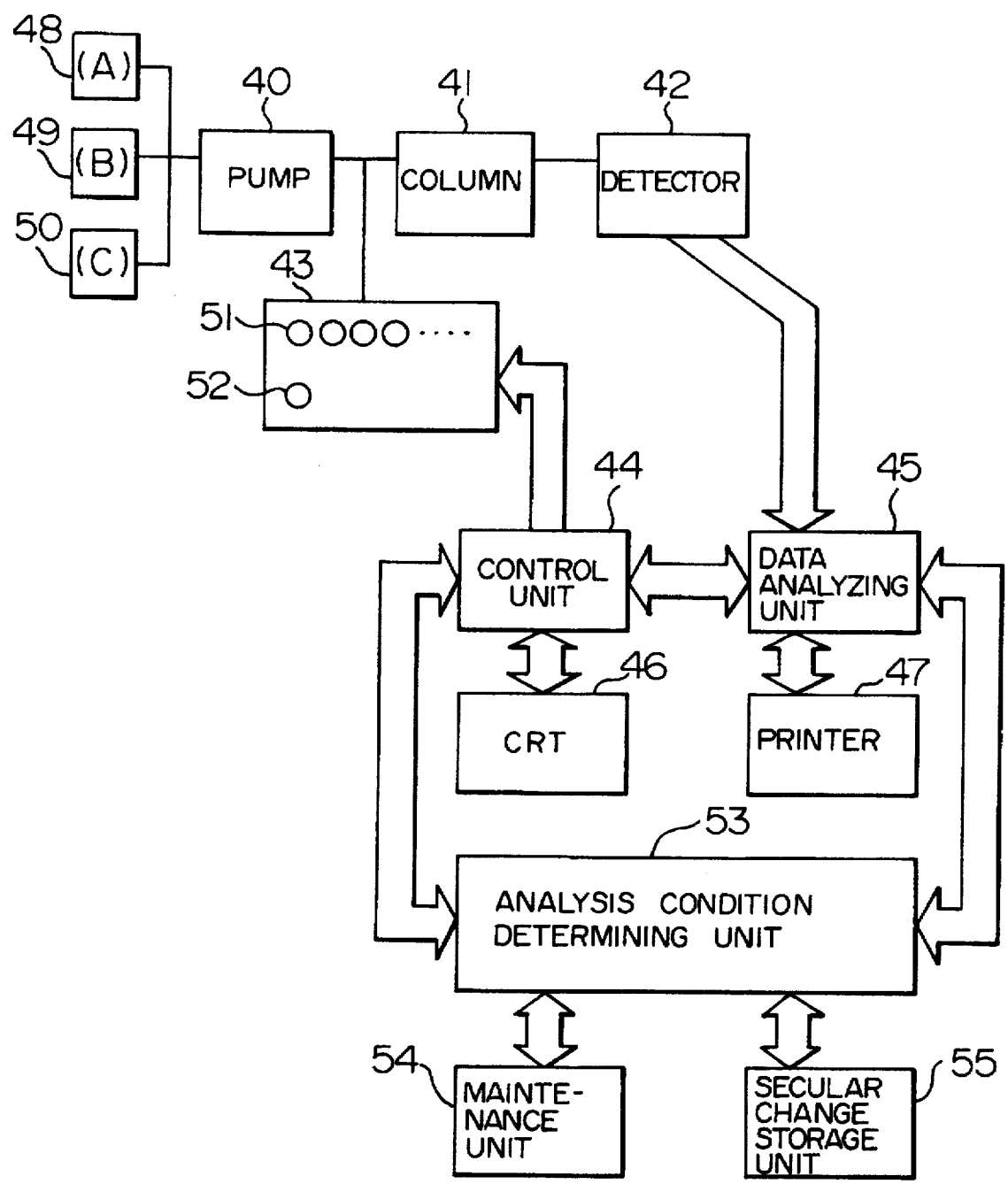
FIG. 1 is a block diagram showing the structure of a chromatography system for analyzing glycated hemoglobin according to an embodiment of the present invention.

FIG. 1 shows the structure of a liquid chromatograph system for analyzing glycated hemoglobin according to an embodiment of the present invention.

Referring to FIG. 1, a pump 40 alternately feeds an eluent (A) 48, eluent (B) 49, and eluent (C) 50 respectively for 1.9, 1.0 and 0.4 minutes at the cycle time of 3.3 minutes, for performing the stepwise (gradient) elution.

A sampler 43 having a movable needle sucks 5 μl of a hemoglobin (Hb) standard sample, dilutes it through hemolyzing, and sends it to a path leading to a column 41. The standard sample 52 as well as the eluent (A) 48 is supplied to the column 41 where the components of the standard sample are separated and identified by a visible photometer 42. The detected data or chromatogram is stored in a memory of a data analyzing unit (data processing unit) 45. Reference numeral 51 represents unknown samples. For the hardware configuration, a glycated hemoglobin analyzer Type L-9100 manufactured by HITACHI, LTD., may be used.

The column 41 is of the same type as disclosed in U.S. patent application Ser. No. 07/896,784 filed on Jun. 9, 1992, now U.S. Pat. No. 5,294,336, which is a continuation application of U.S. patent application Ser. No. 07/578,214 filed on Sep. 6, 1990, now abandoned, and incorporated herein by reference.

The time window method using the system shown in FIG. 1 has been disclosed in U.S. patent application Ser. No. 07/836,599 filed on Feb. 18, 1992, now abandoned, which is incorporated herein by reference. An example of time windows is shown in Table 1.

TABLE 1

| Window | Peak | Retention Time (min) | +/− Allowable Width (min) |
|---|---|---|---|
| 1 | $A_{1a}$ | 0.30 | 0.15 |
| 2 | $A_{1b}$ | 0.30t + 0.06 | 0.20 |
| 3 | F | 0.65t − 0.11 | 0.15 |
| 4 | $1-A_{1c}$ | 1.00t − 0.20 | 0.15 |
| 5 | $A_{1c}$ | 1.60 | 0.40 |
| 6 | $A_0$ | 2.60 | 0.30 |

As described above, a standard sample with known components is analyzed before starting each run. On one of the conditions that the retention time of peak $A_{1a}$ of the standard sample is not within the range from 0.15 to 0.45 minutes, that the retention time of peak $A_{1c}$ is not within the range from 1.20 to 2.00 minutes, and that the retention time of peak $A_0$ is not within the range from 2.30 to 2.90 minutes, the analysis of unknown samples will not be performed but an alarm is issued to the operator. This technique is being disclosed in U.S. patent application Ser. No. 07/763,203 filed on Sep. 20, 1992, now abandoned, which is incorporated herein by reference. The retention times of peaks $A_{1b}$, F, and $1-A_{1c}$ are obtained using the retention time of peak $A_{1c}$. For example, assuming that the retention time of peak $A_{1c}$ is 1.85 minutes, the retention time of peak $A_{1b}$ is 0.30*1.85+0.06=0.62 minutes. Similarly, the retention times of peaks F and $1-A_{1c}$ are calculated to be 1.09 and 1.65 minutes, respectively. In this manner, six windows are set for the analysis of unknown samples. If there are a plurality of peaks in one window, the object peak is selected by the following rules:

(1) A peak having the longest retention time is selected as peak $A_{1a}$ in window No. 1.

(2) A peak having the longest retention time is selected as peak $A_{1b}$ in window No. 2.

(3) A peak having the largest area is selected as peak F in window No. 3.

(4) A peak having the largest area is selected as peak $1-A_{1c}$ in window No. 4.

(5) A peak having the largest area is selected as peak $A_{1c}$ in window No. 5.

(6) A peak having the largest area is selected as peak $A_0$ in window No. 6.

Of the function 0.65t−0.11 for calculating the retention time of peak F shown in the time window Table, the coefficient 0.65 of the first order term and the coefficient—0.11 of the zero order term are determined experimentally. Similarly, the coefficients of the functions for calculating the retention times of peaks $A_{1b}$ and $1-A_{1c}$ are determined. These coefficients are not, therefore, perfectly reliable for the practical analysis where the system, column, and eluent change with each lot and there is some deterioration of the column or the like.

This embodiment discloses the method of correcting these coefficients, or the method of correcting time windows. Data analysis conditions (functions practising the time window method) under which the peaks are identified by the data analyzing unit 45, are set by, and stored in, an analysis condition determining unit 53. A calculation section of the analysis condition determining unit 53 calculates to correct the coefficients of the data analysis conditions (functions) used by the time window method.

Table 2 shows the data of past five standard samples 52 obtained until the analysis of a new run starts. The data, including measured retention times $T_1$ of peak $A_{1c}$, measured retention times $T_2$ of peak F, calculated retention times $T_3$ of peak F from the function (0.65t−0.11), and differences between $T_2$ and $T_3$, at respective time and date, is stored in a secular change storage unit 55.

TABLE 2

| Run | 1 | 2 | 3 | 4 | 5 |
|---|---|---|---|---|---|
| Measured Time/Date | 8/10 11:02 | 8/9 15:15 | 8/9 10:57 | 8/7 12:00 | 8/5 9:00 |
| Measured Retention Time $T_1$ of $A_{1c}$ | 1.80 | 1.50 | 1.60 | 1.70 | 1.40 |
| Measured Retention Time $T_2$ of F | 1.09 | 0.85 | 0.94 | 1.00 | 0.84 |
| Calculated Retention Time $T_3$ of F | 1.06 | 0.87 | 0.93 | 1.00 | 0.80 |
| $T_2-T_3$ | +0.03 | −0.02 | +0.01 | ±0.00 | +0.04 |

Figure 2:
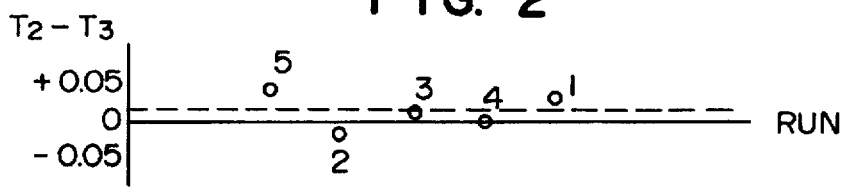
FIG. 2 is a diagram showing the distribution of differences between measured and calculated retention times of peak F.

FIG. 2 is a diagram showing the distribution of differences between measured and calculated retention times $T_2$ and $T_3$. As seen from FIG. 2, $T_2$ is slightly longer than $T_3$.

In a first embodiment, for the correction of the coefficients, the analysis condition determining unit 53 automatically selects five sets of past data from the secular change storage unit 55 to obtain an average value of differences, or a shift amount, and corrects the zero order term coefficient of the function. In this example, the average value +0.22 of differences is added to the initial coefficient—0.11 to change it to a new coefficient—0.09 and obtain a new function 0.65t−0.99.

In a second embodiment, in calculating the average value of differences, the differences are weighted greater for the later measured results.

For example, the shift amount is obtained by the equation (1). In this example, from the calculation given by (2), the function is corrected to 0.65t−0.10.

$$\bar{x} = \frac{\sum_{i=1}^{5} 2^{-i} x_i}{\sum_{i=1}^{5} 2^{-i}} \qquad (1)$$

$$\frac{\frac{1}{2} \times (+0.03) + \frac{1}{4} \times (-0.02) + \frac{1}{8} \times (+0.01) + \frac{1}{16} \times (+0.00) + \frac{1}{32} \times (+0.04)}{\frac{1}{2} + \frac{1}{4} + \frac{1}{8} + \frac{1}{16} + \frac{1}{32}} = +0.01 \qquad (2)$$

This weighting method gives prominence to the later measured results, and is therefore practical from the viewpoint of eliminating the past influence of change in the column and eluent. If the number of past measurements is increased to be more than 5, the average value is less affected by the old measured results. The average value thus obtained is indicated by a broken line (regression line) in FIG. 2.

The automatic correction of the data analysis condition described above may be displayed in the form of a message on a monitoring means such as a CRT 46.

Alternatively, Table 2 or the diagram of FIG. 2 may be displayed on CRT 46 or printed out to a printer 47 for the confirmation by an operator. If the data automatically selected is improper or insufficient, an operator enters an identification number to delete, change, or add data.

Figure 3:
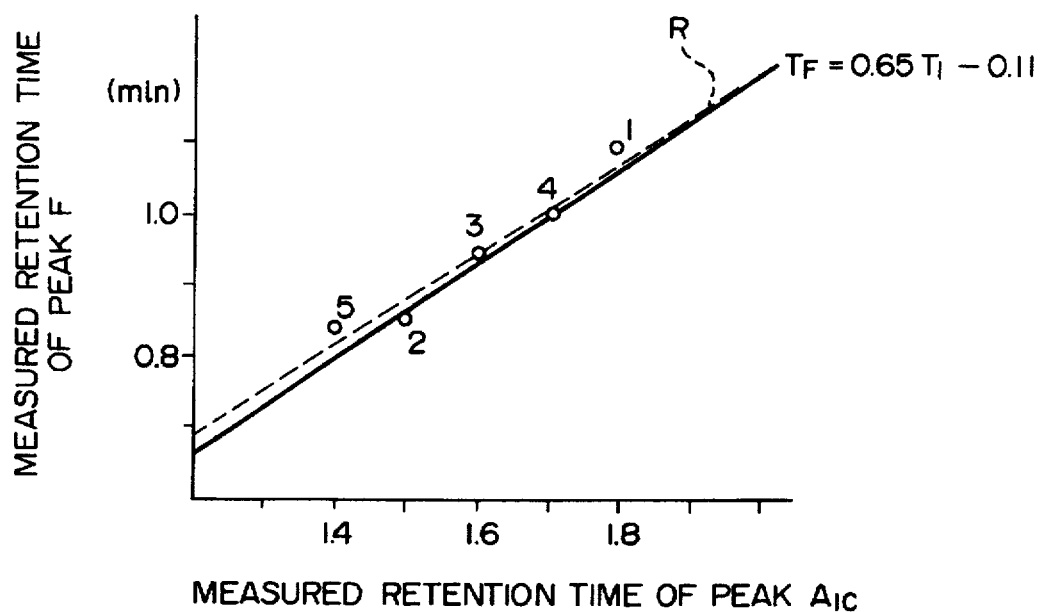
FIG. 3 is a graph showing the relationship between the measured retention times of peak F and peak $A_{1c}$.

In a third embodiment, both the first and zero order term coefficients are corrected. To this end, a regression line R between the measured retention times of peaks F and $A_{1c}$ is obtained as indicated by a broken line, to set the $T_2$-axis intercept of the line R to the zero order term coefficient, and the slope of the line R to the first order term coefficient. The solid line in FIG. 3 is defined by experimentally obtained coefficients. In correcting the coefficients in this manner, the number of data sets is preferably more than 5 in order to avoid a radical change of the first order term coefficient. The regression line is obtained, for example, by the least squares method. The data to be used is sequentially updated to obtain the latest data.

If the obtained correction coefficients change radically from the initial coefficients, there may be a correction error. In such a case, an alarm is issued. As the criterion for issuing an alarm, the time when the first order coefficient changes 20% or more, or the time when the zero order coefficient changes 0.20 minutes or longer, may be set.

In the above description, the sub-peak F and peak $A_{1c}$ have been used by way of example. $A_{1b}$ and 1–$A_{1c}$ may also be used for the coefficient correction of the functions. In the case of 1–$A_{1c}$, however, this peak may not be detected from the standard sample 52. In such a case, data of an unknown sample 51 is used for the coefficient correction, and the analysis condition determining unit 53 processes the data and sends the corrected coefficients to the data analysis unit 45 for the coefficient setting.

The allowable width of each time window may be corrected. For example, the allowable width +/−0.15 minutes of peak F may be changed to a different width such as +/−0.10 and +/−0.20 minutes in accordance with the retention time variation of measured peaks F of several hundreds unknown samples 51. If the allowable width is to be magnified, the magnified width is first used to test whether peak F can be identified properly.

It is also possible to check the functional difference between time windows before and after correction. Namely, one or more peaks to be identified is subjected to the time windows before and after correction. If the peak is identified with the former but is not identified with the latter, or in a reverse case, then an operator is notified of an alarm. In this comparison, retention time of the peak and the time windows are stored in an outer or inner memory device.

Returning back to Table 2, it can be understood that the measured retention time of peak $A_{1c}$ changes greatly although it falls within the allowable range of 1.60+/−0.40 minutes. It has been found from the studies by the present inventors that the retention time of peak $A_{1c}$ of glycated hemoglobin becomes shorter as the number of runs increases. In another embodiment accordingly, an average value of five to twenty sets of past data is calculated for peak $A_{1c}$ in the same manner described above, to update the time window table. The peaks $A_{1a}$ and $A_0$ are calculated also in the same manner.

As described above, the reliability of analyzed results improves as the time window table is updated, while alleviating the burden on an operator. In order to further improve the reliability of analyzed results, it is preferable to narrow the time window width, i.e., the allowable width shown in Table 2. This can be achieved by the embodiment described above. A high reliability can be achieved by using time window tables before and after correction and comparing the analyzed results.

The analysis condition determining unit 53 of the chromatograph system of the above-described embodiments is provided with another function of automatically determining a maintenance condition and automatically correcting a system control condition.

First, the function of automatically determining a maintenance condition will be described, in which a life time of a system component is estimated and a replacement time is notified to an operator. For example, in the case of estimating a life time of a column, the measured column pressure is used as a life time index, and the life time of the column is estimated from a change of the column pressure with time by using various life time functions.

<Differential Coefficient Method>

Figure 4:
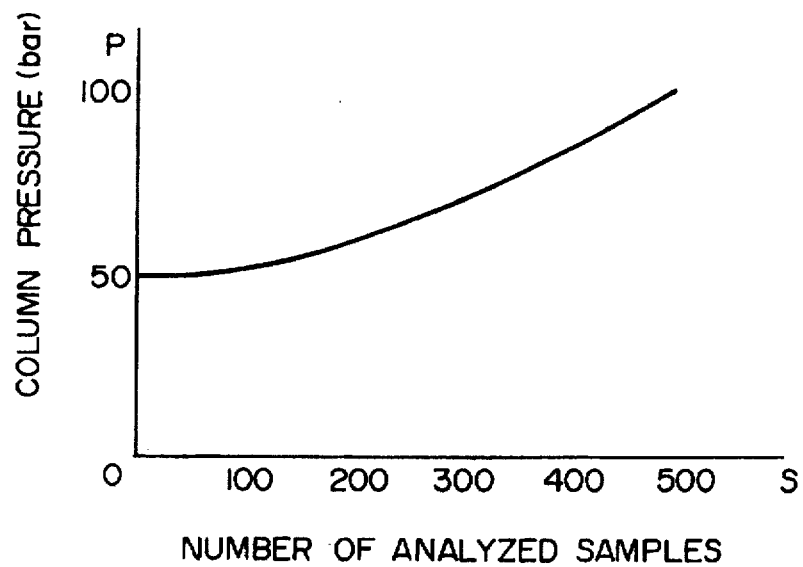
FIG. 4 is a graph showing a change in column pressures used as the criterion of column life prediction.

The column pressure tends to rapidly increase as the number of analyzed samples increases, as shown in FIG. 4. In one embodiment of the life time estimating method, the number S of samples when the column pressure reaches its upper limit Pmax is calculated by using a first order differential value dP/dS (bar/sample) and second order $d^2P/dS^2$ (bar/sample$^2$) at a certain number So of samples, as given by the equation (3):

$$P_{max} = P(S_o) + \left(\frac{dP}{dS}\right)_{S=S_o} (S-S_o) + \frac{1}{2} \left(\frac{d^2P}{dS^2}\right)_{S=S_o} (S-S_o)^2 \quad (3)$$

For example, assuming that Pmax is 100 bar, that the pressure P(So) is 70 bar when the number So of samples reaches 400, that the first order differential value $(dP/dS)_{S=S_o}$ is 0.2 (bar/sample), and that the second order differential value $(d^2P/dS^2)_{S=S_o}$ is 0.002 (bar/sample$^2$), the number S of samples when the column pressure reaches the upper limit pressure Pmax is 500 as given by:

$$100 = 70 + 0.2 \times (S-400) + \frac{1}{2} \times 0.002 \times (S-400)^2 \quad (4)$$

During the period while the 400-th sample is analyzed, it can be estimated that the column pressure will reach its upper limit after 100 more samples. The message of the column replacement time may be displayed on CRT 46 to notify the operator. This method is also applicable to not only a column replacement but also to an in-line filter replacement or card column replacement. However, it is difficult to estimate the replacement time during the period where the first and second order differential values take a value near zero. These differential values will not have large errors.

An example of calculating the differential values are given by the equations (5):

$$\left(\frac{dP}{dS}\right)_{S=S_{1,2}} = \frac{P_1 - P_2}{S_1 - S_2} \quad (5)$$

$$\left(\frac{d^2P}{dS^2}\right)_{S=S_{1,2,3}} = \frac{\left(\frac{dP}{dS}\right)_{S=S_{1,2}} - \left(\frac{dP}{dS}\right)_{S=S_{2,3}}}{S_{1,2} - S_{2,3}}$$

where

-continued $$\begin{cases} S_{1,2} = \dfrac{S_1 + S_2}{2} \\ S_{1,2,3} = \dfrac{S_{1,2} + S_{2,3}}{2} \end{cases}$$

Three data points are required for the second order differentiation. The three data points are represented by ($S_1$, $P_1$), ($S_2$, $P_2$), and ($S_3$, $P_3$) in the order of the latest, later, and late points.

In estimating the life time, the first order differential value at $S=S_1$ is approximated to $(dP/dS)_S = S_{1,2}$, and the second order differential value is approximated to $(D^2P/dS^2)_S = S_{1,2,3}$.

<Analytical Function>

A predetermined function is prepared and corrected at certain time points using past measured data. For example, consider a function $P=Co+C_1\exp(C_2S)$ where P is a pressure (bar), S is the number of samples, Co(bar), $C_1$(bar), and $C_2$(1/sample) are coefficients. The number of samples is reset when the column 41 is replaced by a new one, and starts being counted. The default values of the coefficients are $C_1=10$ (bar) and $C_2=0.003$ (1/sample). The initial value of Co is (initial pressure (bar)—$C_1$). Prior to starting the data sampling, the pump is required to be idled and the pressure after 10 minutes from the operation start of the pump is recorded at each run. An example of the measured data is shown in Table 3, the data being stored in the secular change storage unit 55.

TABLE 3

| Run | 1 | 2 | 3 | 4 | 5 | 6 | 7 |
|---|---|---|---|---|---|---|---|
| Date | 8/1 | 8/2 | 8/2 | 8/3 | 8/4 | 8/6 | 8/7 |
| Pressure | 50 | 51 | 53 | 53 | 55 | 56 | 58 |
| Number of analyzed samples | 0 | 30 | 80 | 90 | 120 | 150 | 190 |

The coefficients of the function are corrected, for example, at the seventh run, by using the pressure data and the numbers of analyzed samples of the past seven runs, to match the past history of data change. In the example of Table 3, the number of samples when the pressure reaches its upper limit of 100 bar can be estimated to be 500. At the end of the seventh run, there is displayed a message that the number of samples which can still be analyzed is 310.

<Pattern Function Method>

The analytical function has been used for the estimation in the above embodiment. Such a particular function is not necessary, but a function representing a typical pattern of representing a pressure increase may be used. An example of this function is a monotone increasing function y=f(x), where y represents the pressure P and x represents the number S of samples. Using this function, P is related to S by:

$$P = Co + C_1 f(C_2 S) \tag{6}$$

where Co(bar) is a constant, $C_1$(bar) is a coefficient representing the degree of pressure change, and $C_2$(1/sample) is a coefficient representing a speed of pressure change per sample.

Discrete sets of values (xi, yi) are stored. The number of points xi is about 20. Each value xi is related to a corresponding value yi. The value between xi and x(i+1) is obtained by interpolation. In just the same manner as the analytical function method, the number of samples is counted after the column 41 is replaced, and the Co, $C_1$, and $C_2$ are corrected at each data measuring point by using the past pressure data in order to match the past history of data change.

The function f(x) is automatically corrected in accordance with the measured data y. The measured discrete sets of values (xi, yi) are replaced by new sets of values including interpolated values which are obtained by using the matched Co, $C_1$, and $C_2$. The measured values (xi, yi) may be weighted by 10% and added to the already obtained values (xi, yi) representing the pressure change pattern so that the pattern is always refreshed to reflect the actual pattern.

The following items may also be estimated.

(1) Retention time: With the increasing or decreasing tendency of the retention time, the time when the retention time exceeds the allowable range can be estimated by the differential coefficient method to request column replacement.

(2) Peak width: An increase of the width (peak area/peak height) of peak $A_{1c}$ of the standard sample 52 can be estimated by the differential coefficient method to request column replacement.

(3) Lamp intensity: With the monotonous increase of lamp intensity, the limit time of the lamp can be estimated by the differential coefficient method to request lamp replacement.

(4) Detector noise/drift value: The time when these values become stable can be estimated by the differential coefficient method to notify the sampling start time.

Figure 5:
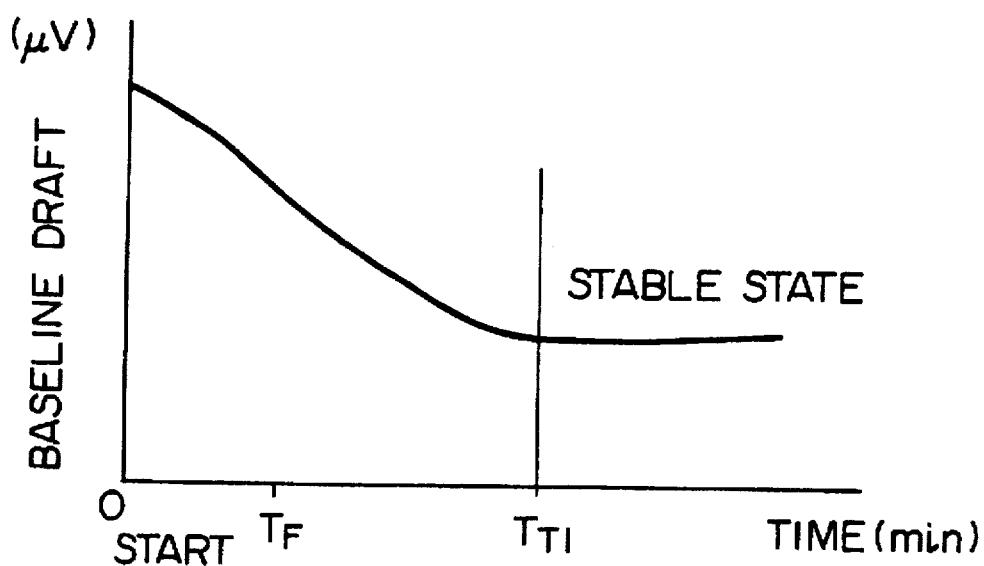
FIG. 5 is a graph showing a baseline drift at the start-up of the system.
Figure 6:
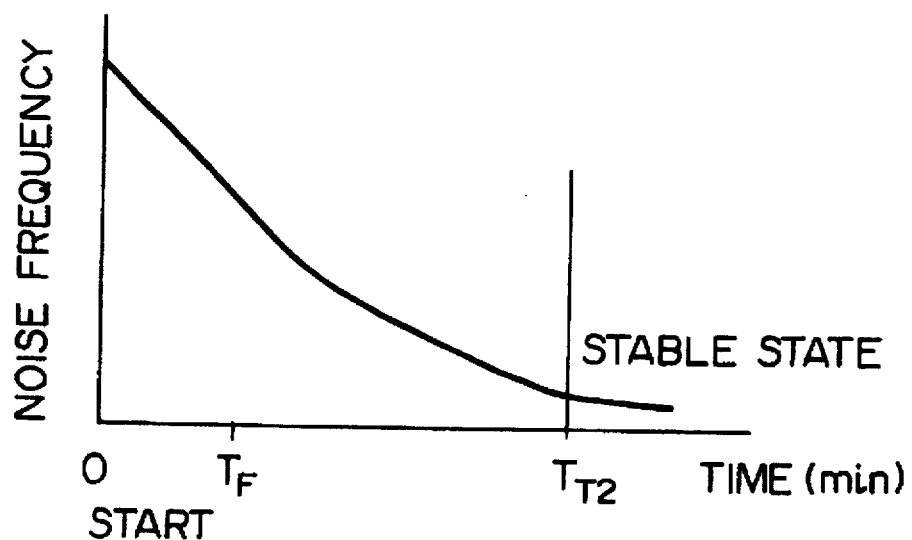
FIG. 6 is a graph showing a change in noise generation frequencies at the start-up of the system.

When the chromatograph system starts its operation, a lamp in the detector turns on. Until the temperature of the lamp becomes stable, the baseline of the detector drifts (refer to FIG. 5) and much noise is generated (refer to FIG. 6).

With a conventional technique, the analysis of standard samples starts when both the baseline voltage and the noise occurrence frequency lower to predetermined threshold values or less.

In the present embodiment, the times when the baseline voltage and the noise occurrence frequency reach the threshold values can be estimated by the differential coefficient method or the like. In the example shown in FIGS. 5 and 6, times $T_{T1}$ and $T_{T2}$ when the baseline voltage and noise occurrence frequency become stable are estimated at time $t_F$, and the later one of the times $T_{T1}$ and $T_{T2}$ is selected as an analysis start enabled time which is notified to the operator. With such a function, a case where the system does not become stable can be also estimated.

The estimation of the analysis start enabled time may be made using either the baseline drift or the noise occurrence frequency as an index.

The above-mentioned estimations are done by the analysis condition determining unit 53. The result thus obtained is delivered to a maintenance unit 54 and a message is issued.

The life time management index may reach the limit value not from its life time itself but from other causes. Such causes may be identified from the secular change data. An example of such identification will be described. Consider for example the chromatograph system wherein the lamp intensity is measured as the deterioration index of the lamp in the detector 42. The lamp intensity decreases monotonously generally in the unit of 100 hours. In this system, an amplifier is used which sets the intensity of a newly replaced lamp to 100 to 200 mV. The lamp intensity is measured at a fixed time after 10 minutes from the start of the pump operation. When the lamp intensity lowers to a predetermined value 50 mV or less, an alarm is issued to the operator to request lamp replacement.

In this embodiment, however, an alarm is not necessarily issued even if the lamp intensity lowers to 50 mV or less. Instead, the maintenance unit 54 first refers to the secular change storage unit 55 to check the secular change of the lamp intensity. If the present value at the predetermined value of 50 mV or less changes abruptly by 20% or more than the value measured at the preceding point, then it is not judged that the lamp life came to the end, but a message of a possibility of a contaminated flow cell is displayed on CRT 46. If the present value at the predetermined value of 50 mV or less does not lower by 20% or more, it is judged that the lamp intensity has lowered gradually to the predetermined value, and so a message of a replacement by a new lamp is displayed.

There is an alternative method of more precisely judging whether the lamp has been deteriorated by its own life time or other causes. Namely, the decrease of the lamp intensity is estimated by the differential coefficient method. If the lamp intensity becomes lower than the estimated value by −10% or more, it is judged that there is another cause except the simple lamp deterioration. Also in the case where the lamp intensity becomes higher than the estimated value by +10% or more, there is a possibility of an abnormal state of other elements.

An abrupt rise of the column pressure can also be checked in the similar manner as above. The retention time, peak width, and injection amount by the sampler 43 using a standard sample having same component compounds, may also be checked in the similar manner.

Lastly, the function of automatically correcting the control conditions will be described. With this function which changes the control conditions slightly, the normal analysis can be continued for a longer time. For example, the case where the retention time of peak $A_{1c}$ of the standard sample becomes gradually short, may be reasoned from the deterioration of the column 41. In such a case, if the pump flow is lowered by 10% when the retention time of peak $A_{1c}$ becomes 1.30 minutes or shorter (this is a second time window), the retention time of peak $A_{1c}$ can be elongated by about 10%. As an alternative of this, the switching time between the eluent (A) 48 and eluent (B) 49 may be delayed by 0.2 minutes.

As a more improved alternative, the control conditions such as flow rate, switching time, column temperature, or in some case, mixture of eluents may be changed slightly so as to regulate the retention time of peak $A_{1c}$ to near 1.7 minutes. In this case, the following two points should be taken into consideration.

(1) Parameters used for peak identification are corrected time sequentially in the manner described above.

(2) A rule is introduced wherein each control condition is slightly changed while suppressing an abrupt change of peak identification parameters, and the condition which provides the most effective results is selected. The chromatograph system itself may be made to learn such a rule.

Specifically, the results obtained in response to a change of the control condition are stored in the secular change storage unit 55, and referred to when the next control condition change is performed. By storing the secular change of the control condition, it is possible to use it for estimation at the next control condition change. The operation of the control condition change is conducted by the analysis condition determining unit 53 and executed by the control unit 44.

Using the secular change data, the embodiments of the present invention provide the following advantageous effects.

(1) The coefficients of a peak identifying function used for the data analysis can be corrected so that a difference between columns, a lot variation of eluents, and a secular change of measured values caused by system components deterioration can be flexibly dealt with.

(2) The life time management index of each system component can be estimated for system maintenance so that a replacement time of each system component can be notified to an operator. Furthermore, a cause other than the expiration of life time can be discriminated when the life time management index fluctuates greatly.

(3) By slightly changing the control condition, it is possible to elongate the replacement time of a system component having a limited life time.

Determination and correction of various conditions necessary for the proper analysis improve the fidelity, precision, and reliability of the analyzed data.

According to one aspect of the present invention, the data analysis condition is automatically corrected in accordance with the secular change of measured values, improving the data analysis precision and ensuring the proper analysis.

According to another aspect of the present invention, the life time is estimated more correctly and the proper component replacement time can be notified. When the life time index takes a predetermined value, it is possible to determine whether it has occurred from the life time itself or from another cause, further improving the system reliability.

According to a further aspect of the present invention, by changing the control condition, it is possible to elongate the component replacement time.

What is claimed is:

1. A method for automatically correcting a measurement condition of a chromatograph system comprising steps of:

a) chromatographically separating and measuring a plurality of runs of samples with the chromatograph system, each run of samples including, first a standard sample followed by unknown samples, to obtain a chromatogram of each of said samples, said chromatogram of each sample having a main peak and a subsidiary peak, said main peak appearing within a first time window defined by a first retention time and a first allowable width, and said subsidiary peak appearing within a second time window defined by a second retention time which is represented by a linear function of said first retention time of said main peak and a second allowable width;

b) determining a main retention time of said main peak and a subsidiary retention time of said subsidiary peak of each sample;

c) setting a regression line between points each represented by the main retention time on an abscissa and by the subsidiary retention time on an ordinate, for the samples of at least one of said runs;

d) basing said first and second time windows for each of said plurality of runs on a set of preceding runs; and d) correcting said linear function by fitting said linear function to said regression line so that said second time window is updated.

2. The method according to claim 1, wherein said set of preceding runs comprises at least five runs.

3. The method according to claim 1, wherein said sample is glycated hemoglobin, said main peak is in correspondence with a component of $A_{1c}$, and said subsidiary peak is in correspondence with at least one of components of F, $1-A_{1c}$, and $A_{1b}$.

4. The method according to claim 1, further comprising steps of:

e) detecting whether said subsidiary peak appears within said second time window not updated;

f) detecting whether said subsidiary peak appears within said second time window updated; and g) indicating when said subsidiary peak does not appear within at least one of said second time windows.

5. The method according to claim 1, further comprising steps of:

e) calculating an average among said main retention times; and f) correcting said first retention time to fit said first retention time to said average so that said first time window is updated.

6. The method according to claim 5, further comprising steps of:

g) detecting whether said main peak appears within said first time window not updated;

h) detecting whether said main peak appears within said first time window updated;

i) detecting whether said subsidiary peak appears within said second time window not updated;

j) detecting whether said subsidiary peak appears within said second time window updated; and k) indicating when at least one of said main and subsidiary peaks does not appear within at least one of said first and second time windows.

7. The method according to claim 6, wherein said set of preceding runs comprises at least five runs.

8. A method for measuring a chromatograph of samples including glycated hemoglobin comprising steps of:

a) chromatographically separating and measuring a plurality of runs of samples with the chromatograph, each run of samples including, first a standard sample followed by unknown samples, to obtain a chromatogram of each of said samples, said chromatogram of each sample having a main peak corresponding to a component $A_{1c}$ of the glycated hemoglobin and a subsidiary peak corresponding to at least one of components of F, $1-A_{1c}$ and $A_{1b}$, said main peak appearing within a first time window defined by a first retention time and a first allowable width, and said subsidiary peak appearing within a second time window defined by a second retention time which is represented by a linear function of said first retention time of said main peak and a second allowable width;

b) determining a main retention time of said main peak and a subsidiary retention time of said subsidiary peak of each sample;

c) setting a regression line between points each represented by the main retention time on an abscissa and by the subsidiary retention time on an ordinate, for the samples of at least one of said runs;

d) basing said first and second time windows for each of said plurality of runs on a set of preceding runs;

e) correcting said linear function by fitting said linear function to said regression line so that said second time window is updated and f) obtaining chromatograms of subsequent ones of said samples by employing the second time window updated.

9. The method according to claim 8, further comprising steps of:

f) calculating an average among said main retention times;

g) correcting said first retention time to fit it to said average so that said first time window is updated; and h) obtaining a chromatogram of said sample by employing the first window updated.

10. A chromatograph system, comprising:

a) a measuring column, having a pressure, to which samples to be measured may be supplied;

b) means for analyzing a number of samples supplied to said column to obtain a chromatogram for each sample, said chromatograph including a retention time and a peak width for each sample measured;

c) means for monitoring at least one monitored parameter selected from a group consisting of said pressure of said column, said retention times and said peak widths;

d) first means for storing a function based on a change in said at least one parameter and said number of said samples analyzed;

e) second means for storing a reference parameter at which said column should be changed;

f) means for correcting said function to fit a set of said monitored parameters to said function;

g) means for calculating a number of samples which can be analyzed before said at least one parameter becomes said reference parameter by referring to the monitored parameters and the function corrected; and h) means for indicating said calculated number of samples.

11. A chromatograph system, comprising:

a) means for analyzing a sample in a column to obtain a chromatogram;

b) means for monitoring a pressure (P) of said column and a number $(S_0)$ of samples analyzed;

c) means for storing an upper limit pressure $(P_{max})$ of said column at which said column should be changed;

d) means for obtaining a first order differential value $(dP/dS)$ and a second order differential value $(d^2P/dS^2)$;

e) means for calculating a number $(S_{max})$ of samples at which a pressure of said column becomes to said upper limit pressure $(P_{max})$ in accordance with the following formula, $$P_{max}=P(S_0)+(dP/dS)_{S=S_0}(S_{max}-S_0)+k(d^2P/dS^2)_{S=S_0}(S_{max}-S_0)^2$$

wherein k is a constant; and f) means for indicating said number $(S_{max})$ of samples thus calculated or a difference between said number $(S_{max})$ calculated and said number $(S_0)$ monitored.

12. A method for measuring a chromatograph of a sample, comprising steps of:

a) analyzing a number of samples supplied to a column, having a pressure, to obtain a chromatogram for each sample, said chromatograph including a retention time and a peak width for each sample measured;

b) monitoring at least one monitored parameter selected from a group consisting of said pressure of said column, said retention times and said peak widths;

c) storing a function based on a change in said at least one parameter and said number of said samples analyzed;

d) storing a reference parameter at which said column should be changed;

e) correcting said function to fit a set of said monitored parameters to said function;

f) calculating a number of samples which can be analyzed before said at least one parameter becomes said reference parameter by referring to the monitored parameters and the function corrected; and g) indicating said calculated number of samples.

13. A method for measuring a chromatograph of a sample, comprising steps of:

a) analyzing a sample to obtain a chromatogram;

b) monitoring a pressure (P) of a column and a number ($S_0$) of samples analyzed;

c) storing an upper limit pressure ($P_{max}$) of said column at which said column should be changed;

d) obtaining a first order differential value (dP/dS) and a second order differential value ($d^2P/dS^2$);

e) calculating a number ($S_{max}$) of samples at which a pressure of said column becomes to said upper limit pressure ($P_{max}$) in accordance with the following formula, $$P_{max}=P(S_0)+(dP/dS)_{S=S_0}(S_{max}-S_0)+k(d^2P/dS^2)_{S=S_0}(S_{max}-S_0)^2$$

wherein k is a constant; and f) indicating said number ($S_{max}$) of samples thus calculated or a difference between said number ($S_{max}$) calculated and said number ($S_0$) monitored.

14. A chromatograph system comprising:

a chromatographic column for separating a sample to obtain a chromatogram having a plurality of peaks, including a first peak and a second peak;

means for storing at least past information relating to said first peak and past information relating to said second peak;

means for correlating between said past information relating to said first peak and said past information relating to said second peak;

means for renewing said correlation based on successively obtained information of said first peak and successively obtained information of said second peak; and means for obtaining information relating to one of said plurality of peaks from detected information relating to another one of said plurality of peaks based on said correlation.

15. A chromatograph system according to claim 14, wherein said past information relating to the first peak and the second peak comprises a retention time or a retention volume.

16. A chromatograph system according to claim 14, wherein said means for correlating establishes said correlation based on a detection of a standard sample.

17. A chromatograph system according to claim 14, wherein said means for storing stores past information relating to said second peak obtained from said past information relating to said first peak by said correlating means.

18. A chromatograph system according to claim 17, wherein said first peak is a main peak and said second peak is a subsidiary peak.

19. A chromatograph system according to claim 18, wherein said correlating means is operative to obtain information concerning said subsidiary peak from information concerning said main peak.

20. A chromatograph system according to claim 14, wherein said correlation is a linear relation.

21. A chromatograph system according to claim 20, wherein said means for correlating establishes said correlation using a polynominal expression.

22. A method for obtaining a chromatogram with a plurality of peaks, including a first peak and a second peak by separating in time a sample through a column, comprising steps of:

storing at least past information relating to said first peak and past information relating to said second peak;

correlating between said past information relating to said first peak and said past information relating to said second peak;

renewing said correlation based on successively obtained information of said first peak and successively obtained information of aid second peak; and obtaining information relating to one of said plurality of peaks from detected information relating to another one of said plurality of peaks based on said correlation.

23. A method according to claim 22, wherein said past information relating to the first peak and the second peak comprises a retention time or a retention volume.

24. A method according to claim 22, wherein said correlation is based on a detection of a standard sample.

25. A method according to claim 22, wherein said past information relating to said second peak is obtained from said past information relating to said first peak.

26. A method according to claim 25, wherein said first peak is a main peak and said second peak is a subsidiary peak.

27. A method according to claim 26, wherein information concerning said subsidiary peak is obtained from information concerning said main peak.

28. A method according to claim 22, wherein said correlation is a linear relation.

29. A method according to claim 28, wherein said correlation is expressed by a polynominal expression.

* * * * *

UNITED STATES PATENT AND TRADEMARK OFFICE
CERTIFICATE OF CORRECTION

PATENT NO. : 5,670,379
DATED : September 23, 1997
INVENTOR(S) : Masahito ITO, et al.

It is certified that error appears in the above-indentified patent and that said Letters Patent is hereby corrected as shown below:

Column 3, line 59, before "0.11" insert a minus sign.

Column 4, line 41, before "0.11" change the dash to a minus and in the same line before "0.09" change the dash to a minus sign.

Column 5, line 42, change "hundreds" to --hundred--.

Column 11, line 60, after "updated" insert a semicolon.

Column 11, line 66, change "f)" to --g)--.

Column 12, line 1, change "g)" to --h)--.

Column 12, line 3, change "h)" to --i)--.

Column 14, line 28, change "aid" to --said--.

Signed and Sealed this

Tenth Day of November 1998

Attest:

BRUCE LEHMAN

*Attesting Officer*      *Commissioner of Patents and Trademarks*